United States Patent [19]

Simonson et al.

[11] 4,328,313

[45] May 4, 1982

[54] METHOD OF PRODUCING A PLAQUE DISPERSING ENZYME

[75] Inventors: Lloyd G. Simonson, Waukegan; Burton L. Lamberts, Libertyville, both of Ill.

[73] Assignee: The United States of America as represented by the Secretary of the Navy, Washington, D.C.

[21] Appl. No.: 232,595

[22] Filed: Feb. 9, 1981

Related U.S. Application Data

[63] Continuation-in-part of Ser. No. 105,315, Dec. 19, 1979, abandoned.

[51] Int. Cl.³ .............................................. C12N 9/24
[52] U.S. Cl. ................................... 435/200; 435/874
[58] Field of Search .......................................... 435/200

[56] References Cited

FOREIGN PATENT DOCUMENTS 1373487 11/1974 United Kingdom ................ 435/200

OTHER PUBLICATIONS

Derwent Abstract 51403 B/28 of Japanese Application No. 131,988.

Chemical Abstracts, vol. 91:106612v (1979) of Japanese Application No. 131,988, Kokai 79/67,092.

*Primary Examiner*—Lionel M. Shapiro

[57] ABSTRACT

A method of producing $\alpha$-1, 3-glucanase by introducing a bacterial culture such as Pseudomonas sp. isolate NRRL B-12324 into an aqueous medium containing a "limit glucan" substrate which is greater than 90 percent $\alpha$-1, 3-glycosidically linked, then allowing growth to take place to accumulate $\alpha$-1, 3-glucanase, and then recovering the enzyme for use as an oral therapeutic agent.

5 Claims, No Drawings

METHOD OF PRODUCING A PLAQUE DISPERSING ENZYME

CROSS-REFERENCE TO RELATED APPLICATION

This is a continuation-in-part application of applicants' copending application Ser. No. 105,315, filed Dec. 19, 1979, now abandoned.

BACKGROUND OF THE INVENTION

The present invention relates to an enzyme useful as an oral therapeutic agent and more particularly to a method of producing α-1, 3-glucan 3-glucanohydrolase which can be used to attack glucans of dental plaque.

Dental plaque is a deposit which accumulates on the teeth and adjacent surfaces in the oral cavity. The plaque is a product of microbial growth resulting from food residues in the mouth. Mucoproteins and minerals present from the saliva and dead cells in the mouth also assist in plaque formation.

Plaque is removed to some extent by effective brushing of the teeth, but the less accessible and more sheltered areas of the mouth which cannot be readily reached by a toothbrush are particularly susceptible to plaque and, eventually, calculus growth. Left unhindered, the plaque increases in size and more tenaciously adheres to the teeth. The bacterial metabolism within the plaque on the tooth surface results in the production of acids, toxins and enzymes which are deleterious to the neighboring oral tissues. There is much evidence pointing to certain bacterial plaques as being the direct cause of dental caries, due to the generation of acids within the plaque structure. In any event plaque is unhealthy and therefore undesirable.

During recent years, it has been found that the organisms often associated with the formation of dental caries are certain oral streptococci belonging to the *Streptococcus mutans* group which contribute to the build-up of plaque and have been implicated in the development of dental caries and periodontal diseases. Specific strains of *Streptococcus mutans* can synthesize adhesive glucans which facilitate adherence of the organisms to tooth surfaces and contribute to the build-up of plaque. The significance of such glucans in relation to dental disease has been demonstrated through various investigations with "glucan synthesis-defective" mutants which have exhibited only low levels of virulence in animal experiments. Other streptococcal strains are additionally thought to synthesize fructan (levan) polysaccharides. Still other Actinomyces strains are major constituents of dental plaque and can be related to both root surface caries and periodontal disease. Such organisms also contribute to the formation of plaque through the synthesis of slimy, extracellular and cell-surface polysaccharides.

The extracellular streptococcal glucans are composed of glucosyl units linked in α-1,3, and α-1,6 configurations. Past attempts to control dental plaque formation with plaque-dispersing glucanohydrolases such as dextranase which hydrolyze 1,6-glucosyl linkages have had only limited success possibly because the dextranase enzymes only partially degrade the glucans while leaving a water-insoluble residue. Recent investigations, in fact, have shown that this residual material is composed primarily of 1,3-linked glycosyl units with relatively few 1,6 linkages. While sources of 1,3 glucanohydrolases have been reported, to our knowledge the enzymes are not commercially available for oral therapeutic use.

Various other attempts have been made to control cariogenic bacteria and the formation of plaque on teeth. For example, fluoride solutions or gels have been used. Treatment with these materials is typically performed in a dental office at periodic, but not frequent, intervals. The primary objective of these treatments is to render the tooth enamel more resistant to the acid action caused by plaque. Such treatments do not, however, result in plaque control for an extended period since plaque reestablishes itself on the teeth shortly after ingestion of food.

Even when the frequency of application of such solutions and gels is increased only partial control has been shown. For example, studies wherein a fluoride-containing solution (1% fluoride concentration) was applied four to five times in the course of a year have demonstrated that this technique had only limited success due to the rapid reestablishment of plaque in the oral cavity. Moreover, the daily application of a fluoride gel by means of a custom-fitted polyvinyl mouthpiece for a period of twenty-one months also showed no substantial change in plaque formation among treated and untreated patients. See "Clinical Anticaries Effect of Repeated Topical Sodium Fluoride Application By Mouthpiece", Journal of the American Dental Association, V. 75, No. 3, September 1967, pp. 638–644.

Other attempts at inhibiting the formation of plaque have also been made. For example, U.S. Pat. No. 3,733,399 describes toothpaste compositions which contain the enzyme invertase as the active ingredient. Another approach is disclosed in U.S. Pat. No. 3,894,147 wherein the application to teeth of a dialkyl pyrophosphate having from about 8 to 14 carbon atoms in the alkyl groups is described as useful in inhibiting plaque formation.

SUMMARY OF THE INVENTION

The present invention is a new method of producing α-1,3-glucanase, as a product of bacterial growth which can be effective in combating dental plaque. The most advantageous procedure involves two stages. In the first stage, a seed culture is prepared by growing *Pseudomonas sp.* isolate NRRL B-12324 in Eugonbroth for 72 hours at a temperature of about 30 degrees C. In the second stage a defined medium containing about 0.1 percent of α-1, 3-linked "limit glucan" is inoculated with the seed culture and the batch culture is incubated at a temperature of 30 degrees C. for four or more days, with aeration of 2.5 liters per minute. After the growth period, the cells are removed from the culture medium by centrifugation and filtration.

It is therefore a general object of the present invention to produce an enzyme which can be effective in combating dental plaque.

Another object of the present invention is to provide a new bacterial method for producing α-1, 3-glucanase.

Other objects, advantages and novel features of the invention will become apparent from the following detailed description of the invention.

DETAILED DESCRIPTION OF THE PREFERRED EMBODIMENT

The present invention provides a method for producing an α-1, 3-glucanase by inducing its production with a "limit glucan" substrate that is more than 90 percent α-1, 3-linked glucan. A microorganism has been isolated from soil compost that produces a true extracellular α-1, 3-glucanase and this isolate is an unidentified species of *Pseudomonas*. The *Pseudomonas* species culture useful for the production of α-1, 3-glucanase has been deposited and made a part of the stock culture collection of the Northern Regional Research Center, U.S. Department of Agriculture, Peoria, Ill. 61604, from which it is available to the public under the number NRRL B-12324.

A seed culture is prepared by growing *Pseudomonas sp.* isolate NRRL B-12324 in Eugonbroth for 72 hours at a temperature of 30 degrees C. The second stage of production involves the inoculation with the seed culture of a batch of defined medium containing the "limit glucan". This batch culture is incubated in a fermentor at a temperature of 30 degrees C. for two or more days with continuous aeration. At the end of the growth period, the cells are removed from the culture medium by centrifugation and filtration. The cell-free supernatant is then cooled and sodium azide is added as a preservative.

The "limit glucan" can be obtained by either of two procedures. One procedure involves growing species of *Streptococcus mutans* or some other suitable microoranism in a broth culture medium (usually chemically defined), obtaining a cell free supernatant, and incubating the supernatant along with a sucrose-phosphate buffer. Next, the insoluble glucan obtained by cell-free synthesis is then treated with a dextranase to degrade all available α-1, 6-glycosidic linkages and the resulting insoluble substrate is a "limit glucan" that is more than ninety percent α-1, 3-linked [Meyer, et al., *Carbohyd, Res.* 66:33–42 (1978)]. The second method of producing this "limit glucan" would involve isolating the specific enzyme or enzyme complex responsible for producing an α-1, 3-rich glucan substrate. This glucan would not need to be dextranase treated to reduce the amount of α-1, 6-glycosidic linkages. The α-1, 3-glucan synthetase preparation might be isolated from other enzymes present in the culture broths by employing standard biochemical separation techniques such as column chromatography, iso-electric focusing, differential solubility and others. The specifically synthesized "limit glucan" should also contain greater than 90% α-1, 3-glycosidic linkages. The essence of the present invention involves the use of such "limit glucans", derived either by dextranase treating the streptococcal glucans or by synthesis using a specific α-1, 3-glucan glucosyl transferase, as substrates to induce α-1, 3-glucan hydrolases.

Practice of a specific embodiment of the present invention is illustrated by the following example.

EXAMPLE

A seed culture is prepared by growing *Pseudomonas sp.* isolate NRRL B-12324 in 10 ml of Eugonbroth for 72 hours at a temperature of 30 degrees C. Then 5L of a defined medium in a 13L Lift Fermentor is inoculated with 5 ml of the 72 hour seed culture and this 5 L batch culture is incubated at a temperature of 30 degrees C. for four days with aeration at 2.5 L/min. The defined medium was prepared by adding DL-Asparagine, 0.01%; NaCl, 0.30%; $MgSO_4$, 0.02%; $NH_4H_2PO_4$, 0.10%; $K_2HPO_4.3H_2O$, 0.10%; and the predominatly α-1, 3-linked "limit glucan", 0.10% to 5L of deionized water. The final pH of the medium was adjusted to pH 7.0 with 1 N NaOH. A vitamin and trace element solution (50 ml) was filter sterilized and added to the autoclaved medium after cooling to room temperature. The vitamin and mineral stock solution was prepared by adding K1, 100 mg; boric acid, 10 mg; ammonium molybdate, 10 mg; $MnSO_4$, 10 mg; $FeSO_4$, 50 mg; Thiamine HCl, 200 mg; riboflavine, 200 mg; pyridoxine, 200 mg; nicotinic acid, 200 mg; para-aminobenzoic acid, 200 mg; calcium pantothenate, 200 mg; inositol, 10 mg; biotin, 2 mg; to deionized water in quantities sufficient for a final one liter volume.

At the end of the growth period, the cells are removed from the culture medium by centrifugation and filtration through a 0.2 νm membrane filter (Gelman Instruments Co.). The cell-free supernatant is cooled to 4° C. after adding 0.08% sodium azide as a preservative. The α-1, 3-glucanase is not a constitutive enzyme of the *Pseudomonas sp.* isolate NRRL B-12324. Therefore, the presence of the "limit glucan" is necessary for the adaptive induction of this enzyme. When the organism is cultured in the presence of dextran, no corresponding dextranase was produced. The optimum temperature for both growth and α-1, 3-glucanase production is near 30° C.

The α-1, 3-glucanase can be further concentrated and purified by ultra-filtration using a 1000 molecular weight ultrafilter. The ultrafiltrate can be purified further by dialysis against 0.01 M potassium phosphate buffer. The enzyme can also be precipitated by adding cold acetone (−10° C.) to a final 50% (v/v) concentration or by adding an equal volume of saturated ammonium sulphate. Further purification can be obtained by chromatography on a Bio-Gel P-150 column (BIO-RAD Laboratories). The enzyme elutes in the void volume of this column.

α-1, 3-glucanase was made at the Naval Dental Research Institute, Great Lakes, Illinois, by the method disclosed in the above-recited EXAMPLE and the pH optimum for the α-1, 3-glucanase was found to be near pH 5.0 and the temperature optimum for the hydrolase reaction was near 56° C. The stability of the enzyme was measured by storing the enzyme at 4°, 30°, and 37° C. for 8 days. The enzyme retained 75–79% of its activity under those conditions. When the enzyme is dialyzed against deionized water, it will adhere to hydroxyapatite. However, this adherence is weak since it will elute from the hydroxyapatite with a 0.01 M potassium phosphate buffer. No inorganic ions are required for activity since the addition of 0.02 M ethylenediaminetetraacetic acid did not greatly reduce its hydrolytic activity relative to a control. Complete enzymatic inhibition of activity was observed with 0.02 M ionic concentrations of $Pb^{2+}$, $Fe^{2+}$, $Fe^{3+}$, $Ag^+$, and $Hg^+$, while 0.02 M $Zn^{2+}$ ions caused a 46% decrease in enzymatic activity. The enzyme appears to be specific for α-1, 3-linked glucans. It showed no activity towards dextran (primarily an α-1, 6-linked glucan) nor soluble potato starch (primarily an α-1, 4-linked glucan).

The hydrolytic end products of α-1, 3-glucanase action on the "limit glucan" were analyzed by column chromatography using a Sephadex G-15 column (Pharmacia). The principal end products recovered were a tetra- and disaccharide (22% each) with lesser amounts of a trisaccharide (14%) and the monosaccharide glucose (5%). The void volume contained nearly 37% of the polysaccharide recovered. The α-1, 3-glucanase was able to solubilize 25% of a *Streptococcus mutans* strain K-1R insoluble B dextranase treated "limit glucan" after incubating for 5 days at 37° C. The end products were also analyzed by proton NMR. The results strongly indicate true α-1, 3-glucanase activity. The α-1, 3-glucan hydrolase which was produced was found to be especially capable of hydrolyzing α-D-1, 3-linkages adjacent to α-D-1, 3-neighboring linkages. The action of the enzyme is probably endohydrolytic based on these end product analyses.

The α-1, 3-glucanase activity was determined by an assay involving the use of a "limit glucan" substrate described earlier which was then modified by complexing it with Cibacron Blue Dye [J. Dent. Res. 58:104 abstract No. 47 (1979)]. The enzymatic degradation of the glucan releases soluble blue-complexed products which can be measured with a spectrophotometer at an optimal wavelength near 620 nm. The "limit glucan" was complexed with Cibacron Blue F3GA (Pierce Chemical Co.) by a procedure described by Bohme et al. [J. Chromatog. 69:209–214 (1972)]. The resulting blue glucan substrate was added to 0.2 M sodium acetate buffer, pH 5.5 (1 mg/ml) for the standard assay. The assay procedure was found to be a linear function under certain conditions of time and enzyme concentration. A 0.5 ml solution of enzyme was added to 3.0 ml of blue dye substrate solution and incubated at 37° C. for 3 hrs. The reaction was stopped by adding 2 volumes of 95% ethanol to 1 volume of the assay mixture. The precipitate was recovered by centrifugation and the optical density of the supernatant was measured with spectrophotometer at 620 nm. The instrument was blanked against an ethanol precipitated water-substrate supernatant.

The assay procedure was used to compare the 60-1, 3-glucanase production by our method with that of a published method involving the use of a fungal culture [Proc. IV International Fermentation Symposium: Ferment. Technol. Today, 735–742]. The fungal culture, *Cladosporium resinae* QM7998, was grown in the *Trichoderma viride* salts medium with mannitol as described in the reference. Our method was found to elicit 1.2 times greater α-1, 3-glucanase levels per ml of culture media in two days than was produced by the fungal method in 15 days. It can thus be seen that an improved method is provided for producing α-1, 3-glucanase which can be used as an effective oral therapeutic agent.

Obviously many other variations and modifications of the present invention are possible in the light of the above teachings. It is therefore to be understood that within the scope of the appended claims the invention may be practiced otherwise than as specifically described.

We claim:

1. A method for producing a plaque-dispersing α-1, 3-glucan 3-glucanohydrolase (1,3-glucanase) enzyme which comprises cultivating a bacterial culture of the strain Pseudomonas NRRL B-12324 in an aqueous medium containing a "limit glucan" substrate which is greater than 90 percent α-1, 3-glycosidically linked, then allowing growth until the medium contains an accumulation of 1,3-glucanase and then recovering said enzyme.

2. A method for producing a plaque-dispersing 1,3-glucanase enzyme as set forth in claim 1 wherein said α-1, 3-limit glucan is derived from a dextranase-treated water insoluble glucan from *Streptococcus mutans*.

3. A method for producing a plaque-dispersing 1,3-glucanase enzyme which comprises cultivating a strain Pseudomonas NRRL B-12324 in an aqueous medium containing a "limit glucan" substrate which is greater than 90 percent α-1, 3-glycosidically linked at a temperature of about 30 degrees C. for a period of at least one day and then recovering said enzyme.

4. A method for producing a plaque-dispersing 1,3-glucanase enzyme as set forth in claim 3 wherein said α-1, 3-limit glucan is derived from a purified α-1, 3-glucan synthetase preparation.

5. A method for producing a plaque-dispersing 1,3-glucanase enzyme as set forth in claim 3 wherein said α-1, 3-limit glucan is derived from a dextranase-treated water insoluble glucan from *S. mutans*.

* * * * *